(12) United States Patent
Creaturo

(10) Patent No.: US 10,857,299 B2
(45) Date of Patent: Dec. 8, 2020

(54) SAFETY SYRINGE AND SAFETY DOSE COMBINATION KIT

(71) Applicant: Parenteral Technologies, LLC, Siesta Key, FL (US)

(72) Inventor: Michael A. Creaturo, Siesta Key, FL (US)

(73) Assignee: Parenteral Technologies, LLC, Siesta Key, FL (US)

( * ) Notice: Subject to any disclaimer, the term of this patent is extended or adjusted under 35 U.S.C. 154(b) by 49 days.

(21) Appl. No.: 15/988,461

(22) Filed: May 24, 2018

(65) Prior Publication Data

US 2018/0264197 A1 Sep. 20, 2018

Related U.S. Application Data

(63) Continuation of application No. 14/877,349, filed on Oct. 7, 2015, now Pat. No. 9,987,430, which is a continuation of application No. 13/748,859, filed on Jan. 24, 2013, now Pat. No. 9,192,723.

(60) Provisional application No. 61/591,683, filed on Jan. 27, 2012.

(51) Int. Cl.
*A61M 3/00* (2006.01)
*A61M 5/31* (2006.01)
*A61M 5/00* (2006.01)
*A61M 5/315* (2006.01)

(52) U.S. Cl.
CPC .......... *A61M 5/3129* (2013.01); *A61M 5/002* (2013.01); *A61M 5/31511* (2013.01); *A61M 2005/3126* (2013.01); *A61M 2205/6009* (2013.01)

(58) Field of Classification Search
CPC .. A61M 2205/6081; A61M 2005/3125; A61M 5/31556; A61M 2005/3126; A61M 2205/6063; A61M 2205/60; A61M 5/002; A61M 5/3129; A61M 5/31511
See application file for complete search history.

(56) References Cited

U.S. PATENT DOCUMENTS

| 2,432,605 | A | 12/1947 | Barach |
| 6,413,241 | B1 | 7/2002 | Slishman |
| D545,429 | S | * 6/2007 | Hays ........................... D24/114 |

(Continued)

FOREIGN PATENT DOCUMENTS

WO 2004069314 A1 8/2004

OTHER PUBLICATIONS

Jun. 6, 2013 International Search Report and Written Opinion of International Application No. PCT/US2013/022926, 12 pages.

*Primary Examiner* — Rebecca E Eisenberg
(74) *Attorney, Agent, or Firm* — Suiter Swantz pc llo

(57) ABSTRACT

A syringe calibrated for use with a predetermined medication and including a barrel, a plunger received through an end of the barrel and movable relative thereto, a tip disposed at one end of barrel and configured to be affixed to a device compatible for use with the syringe, a dosage schedule of the predetermined medication marked on the syringe and expressed as a ratio of a patient characteristic to a dosing unit of measurement, a first set of dosing indicia marked on the syringe and expressed as the predetermined patient characteristic, and a second set of dosing indicia marked on the syringe and expressed as the dosing unit of measurement.

20 Claims, 9 Drawing Sheets

(56) References Cited

U.S. PATENT DOCUMENTS

| | | |
|---|---|---|
| 2002/0010429 A1 | 1/2002 | Jack, Jr. |
| 2002/0087121 A1 | 7/2002 | Slishman |
| 2002/0088131 A1 | 7/2002 | Baxa et al. |
| 2004/0024368 A1 | 2/2004 | Broselow |
| 2004/0024372 A1 | 2/2004 | Grogan |
| 2009/0143745 A1 | 6/2009 | Langan et al. |
| 2009/0185973 A1 | 7/2009 | Gorny |
| 2009/0264815 A1 * | 10/2009 | Grogan, Jr. ............... A61J 1/00 604/78 |
| 2010/0130961 A1 | 5/2010 | Tucker |

* cited by examiner

CROSS-SECTIONAL VIEW
I-I

CROSS-SECTIONAL VIEW
II-II

CROSS-SECTIONAL VIEW
III-III

SAFETY SYRINGE AND SAFETY DOSE COMBINATION KIT

RELATED APPLICATIONS AND INCORPORATION BY REFERENCE

This continuation application claims priority from U.S. application Ser. No. 14/877,349 filed Oct. 7, 2015, which is a continuation of U.S. application Ser. No. 13/748,859 filed Jan. 24, 2013 now issued as U.S. Pat. No. 9,192,723, which claims priority from U.S. Application No. 61/591,683 filed Jan. 27, 2012, the entirety of each incorporated by reference herein.

FIELD OF THE INVENTION

The present invention is related, generally, to the field of medicine delivery apparatuses, systems and methods. More specifically, embodiments of the present invention are related to articles, systems, and methods that are used in the administration of medications to patients, particularly via syringe.

BACKGROUND

Medical Administered Errors ("MAE") are occurring in the field of health care at an epidemic proportion, with statistical figures that are staggering. For instance, more people die in a given year as a result of medical errors than from motor vehicle accidents (43,458), breast cancer (42,297), or AIDS (16,516), according to the Centers for Disease Control and Prevention (National Center for Health Statistics) Births and Deaths: Preliminary Data for 1998. National Vital Statistics Reports. 47(25):6, 1999.

The United States Food and Drug Administration ("FDA") evaluated reports of fatal medication errors that it received from 1993 to 1998 and found that the most common types of errors occurred as the result of the injection of medication. These errors included: the administration of an improper dose (41 percent); the administration of the wrong medication (16 percent); and the use of the wrong route of administration (16 percent). The FDA also notes in a study that medication errors injure approximately 1.3 million people annually in the US alone. Children are considered the most vulnerable population because their smaller body masses make them more sensitive to overdoses or under-doses of medication, which could result in the ineffective treatment of the underlying condition, adverse reaction, illness, and even death.

In other reports it has been noted that medication errors occur in approximately one out of every five doses given in hospitals. These and other medication errors reported to the FDA stem from poor communication; misinterpreted handwriting; drug name confusion; drug strength, inaccurate dosage calculation, confusing drug labeling and packaging; lack of employee knowledge; and lack of patient understanding about a drug's directions.

In 2006, The National Committee of Science conducted a study entitled Preventing Medication Errors. The Committee estimated that, on average, a hospital patient is subject to at least one medication error per day, with considerable variation in error rates across facilities. Estimates of incidences of preventable ADE range from 380,000 to 450,000 annually in acute care hospitals alone.

The Institute of Medicine (TOM) released a report in November 1999, entitled "To Err is Human: Building a Safer Health System." According to the report, between 44,000 and 98,000 deaths may result each year from medical errors in US hospitals alone.

The resulting financial impact to the healthcare industry in the United States, according to the American Academy of Pediatrics ("AAP"), is estimated to exceed $100 billion annually. In addition, the AAP reports that "incorrect dosing is the most commonly reported error, including computation and dosage intervals."

Clearly studies consistently show the consolidation and preparation of the correct components and the subsequent correlation and calculation of an injectable medication for a particular patient are the direct cause of the leading MAEs and continues to be a extremely procedurally challenging issue for the health care industry. These errors are exacerbated based in large part by confusion of medications with similar names and labels, different dosages of the same medications, medications with same name yet measured in different unit strengths, calculation of dosage to patients weight or more complex calculations, such as, for example, dosage to body surface area, pediatrics and renal impaired reduced dosage calculated from adult weight dose, different diluents for different routes of administration even for the same medication, multiple diluents, various dilution steps, measurements and calculations for a single medication, all intermixed with a fast pace, high stress environment, coupled with extended working hours, and emergency procedures to name a few. These variables and elements, combined within this environment, will continue to accelerate user errors and exacerbate the already confusing process associated with correctly preparing an administering an injectable medication.

SUMMARY OF THE INVENTION

An invention that prevents these persistent errors from occurring during these vital procedures or that completely eliminates the procedures by replacing them with passive safety systems and devices to accomplish the same by the same administration of the medication by the same acceptable industry standards, would save countless lives.

It is the purpose of this invention to substantially eliminate these leading causes of MAE by substantially completely eliminating the current procedures that users must follow in order to consolidate and correlate the correct components of apparatuses for the administration of medication to patients and to substantially eliminate the need for users to perform calculations and/or measurements to determine the amount of diluent(s) for the medication and all procedures for any calculation of the dosage of the medication to a specific patient weight or body surface area.

Embodiments of the present invention are directed to new and improved apparatuses, kits, designs and methods for administering medication through pharmaceutical syringes, or other apparatuses designed to increase efficiency, substantially eliminate multiple procedural user steps, improve patient-specific precise dosing and to substantially prevent or eliminate MAE, while significantly reducing the overall costs associated with the administration of medicine.

In one embodiment, the present invention is directed to a method for extracting a medication comprising the steps of providing a medication in a medication container, providing a first syringe, with the first syringe comprising an indicia relating to a recommended dosage of the medication. The container may be a vial, an ampoule, or any suitable medicinal container. The need for calculations or correlations of a medication dosage to a patient's weight or body surface area are obviated, as a portion of the first syringe is presented to or delivered into the container, and the first syringe is filled to a recommended dosage with the injectable medication, and once again obviating the need for calculations or correlations of a medication dosage to a patient's weight or body surface area. The injectable medication is then administered into a patient. Preferably, the dosage is indicated on the syringe in volumetric dosage, and preferably, the dosage is indicated in units such as, for example, CC, IU, MG, MCG, and ML to patient weight or body surface area Preferably, the patient weight or body surface area is indicated in units including, for example, KG, LB, G and $m^2$.

In a further embodiment, the present invention further comprises the steps of providing a lyophilized or dry-filled composition in the medication container, providing a diluent in a diluent container, and reconstituting the lyophilized or dry filled composition by providing the diluent to the lyophilized or dry-filled composition.

In a still further embodiment, a preferred method further comprises the steps of providing a diluent container to reconstitute the medication, and wherein the first syringe is volumetrically calibrated with measurement indicia and recommended dosage, providing a second syringe, said second syringe volumetrically calibrated with measurement indicia for the diluent, extracting a correct amount of diluent from the diluent container using the second syringe, injecting the extracted diluent from the second syringe into the medication container, reconstituting the medication; and obviating the need for calculating or correlating the medication, or the syringe to a patient's weight or body surface area.

According to the present disclosure, a syringe is disclosed comprising a barrel comprising at least two substantially permanent calibrated measurement indicia, wherein a first indicia comprises a volumetric dosage of a medication that correlates a recommended dosage to a second permanent measurement indicia for a patient's weight or patient's BSA. The recommended dosage is a manufacturer's recommended dosage of the medication, and preferably, the barrel of the syringe comprises a third or multiple substantially permanent calibrated measurement indicia correlated to a manufacturer's maximum dosage to a patient's weight or patient's BSA. According to further embodiments, the barrel comprises a substantially permanent calibrated measurement indicia correlating to a specific dosage schedule of a specific medication to patient weight. The present disclosure further contemplates that desired printed information identifying a medication on a syringe component can exist on one of more of any syringe component including a barrel, a plunger nested within a barrel, and combinations thereof. The information includes: medication name, medication strength, medication dosage-to-weight, and combinations thereof. The printed information is preferably the name of medication, the strength of medication, medication dosage-to-weight, and combinations thereof.

The syringe may be pre-filled with a medication, with the syringe comprising a substantially permanently calibrated measurement indicia correlating the dosage of the medication to a patient's weight. The plunger is preferably dimensioned to nest within the barrel, and plunger may be permanently calibrated with measurement indicia correlating the dosage of the medication to the patient weight.

The present disclosure is also directed to a kit comprising a pre-measured volumetrically scaled medication container having a preselected volume and a syringe having a volume capacity substantially equivalent to the preselected volume and a barrel comprising at least two substantially permanent calibrated measurement indicia, wherein a first indicia is a recommended dosage that specifically correlates the recommended dosage to a second substantially permanent measurement indicia for a patient's weight. The kit is preferably pre-packaged and tamper-resistant. The container is selected from the group including a vial, an ampoule, and combinations thereof. The syringe is filled with a volume from the medication container to a maximum calibrated measurement indicia without any calculations or correlations. The measurement indicia are calibrated to deliver the correct doses of the recommended dosage of a specific medication to a particular patient weight without any calculations or correlations.

In addition, the present disclosure is directed to a kit comprising a medication in a medication container and a first syringe corresponding to the medication container, with the medication volume scaled in the medication container to correlate with the first syringe, and the syringe comprising an indicia calibrated to deliver the medication according to a recommended medication dosage to a patient weight or body surface area.

In addition, the present disclosure is directed to a method for delivering medication to a patient via a syringe comprising the steps of providing a medication in a container providing a syringe comprising calibrated measurement indicia and a recommended or maximum dosage of the medication without the need for any calculations or correlations of the medication dosage to the patient's specific weight, correlating the volume of the medication in the container to specifically correlate the medication to calibrated measurement indicia of the syringe, delivering a portion of the syringe into the container and filling the syringe to a recommended dosage of the medication without the need for any calculations or correlations of the medication dosage to the patient's specific weight and administering the medication into a patient. The syringe preferably is filled to a recommended or maximum dosage of the medication such that the indicia would correctly administer a recommended dosage-to-weight volume without additional calculations. Preferably the volume of the syringe is correlated through reducing the interior diameter of the barrel core to provide an enlarged indicia on the syringe for a reduced patient weight range and for better visibility, accuracy, and lower incremental doses for smaller volumes injections.

Still further, the present disclosure relates to a method for extracting a medication from a container comprising the steps of providing a medication in a container, providing a syringe comprising a calibration relating to the medication and featuring a first volumetric indicia for dosage strength and a second indicia relating to a recommended patient weight or body surface area (BSA). The calibration does not require any further calculations or correlations of the medication dosage to the patient's specific weight. A portion of the syringe is delivered into the container and the syringe is filled to a recommended dosage with the injectable medication without the need for any calculations of correlations of the medication dosage to the patient's specific weight. The injectable medication is then administered to the patient via the syringe.

In one embodiment, the present invention substantially eliminates as many sources of human error as possible in the administration of injectable medications by eliminating the user's need to perform separate calculations and correlations without deviating from industry acceptable practices or the instructions for administration issued by the manufacturer of the medication.

More particularly, embodiments of the present invention completely remove and eliminate the practices and procedures currently used in the healthcare industry that are responsible for the primary causes of Medical Administered Errors by injectable administration. Specifically, embodiments of the present invention eliminate the procedures, methods, research and verification ordinarily conducted by users through the consolidation of, for example, the correct medication for patient class, the correct diluent(s), syringe(s) and needle(s) for the medication, correlation of the correct diluent(s), syringe and needle for the route of administration of the particular medication, calculation of correct amount of diluent for the medication, as well all calculations necessary to administer the correct drug dosage to the specific patient, etc.

In a preferred embodiment of the present invention, a syringe is designed and volumetrically calibrated for use with a specific medication within a combinatorial tamper-resistant kit, whereby the syringe is used to load and administer the dosage that the manufacturer recommends for the patient's particular body weight, or body surface area (BSA), solely through its design. The syringe does this without requiring the user to perform any calculations, make any correlations or use any other components and/or devices. The syringe's volumetrically calibrated substantially permanent indicia indicate the amount of medication to be administered to a patient of a given weight or more complex patient feature and measurement, such as, for example, body surface area (BSA) measured in $m^2$, for ultra-sensitive, precise dosage used in biologics and oncology medications, among others. No additional steps or devices are necessary.

More particularly, embodiments of the present invention are directed to a process for extracting an injectable medication by providing a composition to be injected and a syringe comprising recommended and/or maximum dosage-to-weight indicia of the injectable medication. The syringe is filled with injectable medication from the container (vial, ampoule, etc.) to a recommended or maximum dosage (based on the body weight of the patient) of the injectable medication without the need for any calculations or correlations of the medication's dosage schedule to the patient's specific weight and administered into the patient.

Further embodiments of the present invention are directed to a pre-packaged, tamper-resistant kit comprising a pre-measured, volumetrically calibrated, scaled container that specifically correlates the medication dosage strength and/or volume to the indicia on the syringe within the kit. The syringe comprises a barrel bearing at least two permanent calibrated measurement indicia, wherein the first indicia is a recommended dosage that specifically correlates the recommended dosage to a second permanent measurement indicia for a patient's weight. The medication may be scaled to individual patient range within the kit correlating to the calibrated syringe indicia for that targeted patient range, provides a precise lower dose calibration scale, reduces the potential severity of an overdose, and also provides for a patient-specific injection range that significantly reduces waste medication left within the container associated by typical industry standard practices.

Still further embodiments of the present invention are directed to a method for delivering medication to a patient via a syringe by providing a combination kit comprising a medication in a container, and providing a syringe, said syringe comprising calibrated measurement indicia and a recommended or maximum dosage of the medication without the need for any calculations or correlations of the medication dosage to the patient's specific weight or BSA. The volume of the medication is calculated in the container to specifically correlate the medication to calibrated measurement indicia of a syringe A portion of the syringe is directed into the container and filled to a recommended dosage of the medication without the need for any calculations or correlations of the medication dosage to the patient's specific weight, and the medication is administered into the patient.

A further embodiment of the present invention is directed to a method for delivering medication to a patient via a syringe by providing a medication in a container and providing a syringe that bears calibrated measurement indicia for that particular medication that is then calibrated and correlated to another indicia measurement for a recommended and/or maximum dosage to patient weight or BSA of the medication without the need for the user to perform any calculations or correlations of the medication dosage to the patient's specific weight. This enables the user to insert a portion of the syringe into the container and fill the syringe to a recommended or maximum dosage of the medication based upon the patient's body weight such that the indicia would allow the syringe to be correctly loaded with the recommended dosage-to-weight volume for the medication without additional calculations.

In yet a further embodiment of the present invention, the syringe barrel may be manufactured to have a specific core diameter or other volumetric calibration adjustment to provide enlarged elongated targeted indicia on the syringe for specific patient weight or BSA range, thus providing better visibility, accuracy, and lower incremental calibration doses for smaller volumes injections, such as for neonatals and pediatrics.

BRIEF DESCRIPTION OF THE DRAWINGS

The accompanying Figures illustrate aspects of embodiments of the present invention. These, together with the description illustrate the objects, advantages and principles of embodiments of the present invention. In the Figures:

FIG. 10 illustrates a syringe according to embodiments of the present invention, the syringe having the same outer diameter as the 3 ml volume syringe of FIG. 9, yet through it calibrated inner barrel offering enhanced visibility as it extends a 1 ml volume through the full indicia of the syringe in lower incremental doses for increased precision.

DETAILED DESCRIPTION

According to one embodiment of the present invention, a syringe or other apparatus for medicinal administration (hereinafter referred to as a "syringe") may be designed for use with a specific medication. The syringe is preferably clearly and conspicuously labeled to indicate the name of the medication it is intended to administer. In one preferred embodiment, the syringe has a calibration scale on one or more of its barrel, its plunger, or other component that is marked in indicia of a patient characteristic, such as, for example, patient weight or body surface area (BSA, measured as $m^2$). This enables the user to administer a manufacturer's recommended dosage of a subject medication, for example, strictly according to a patient's weight, or other desired characteristic, without performing any mathematical calculations, computations or correlations, etc. (See FIG. 5, feature 400).

Figure 1:
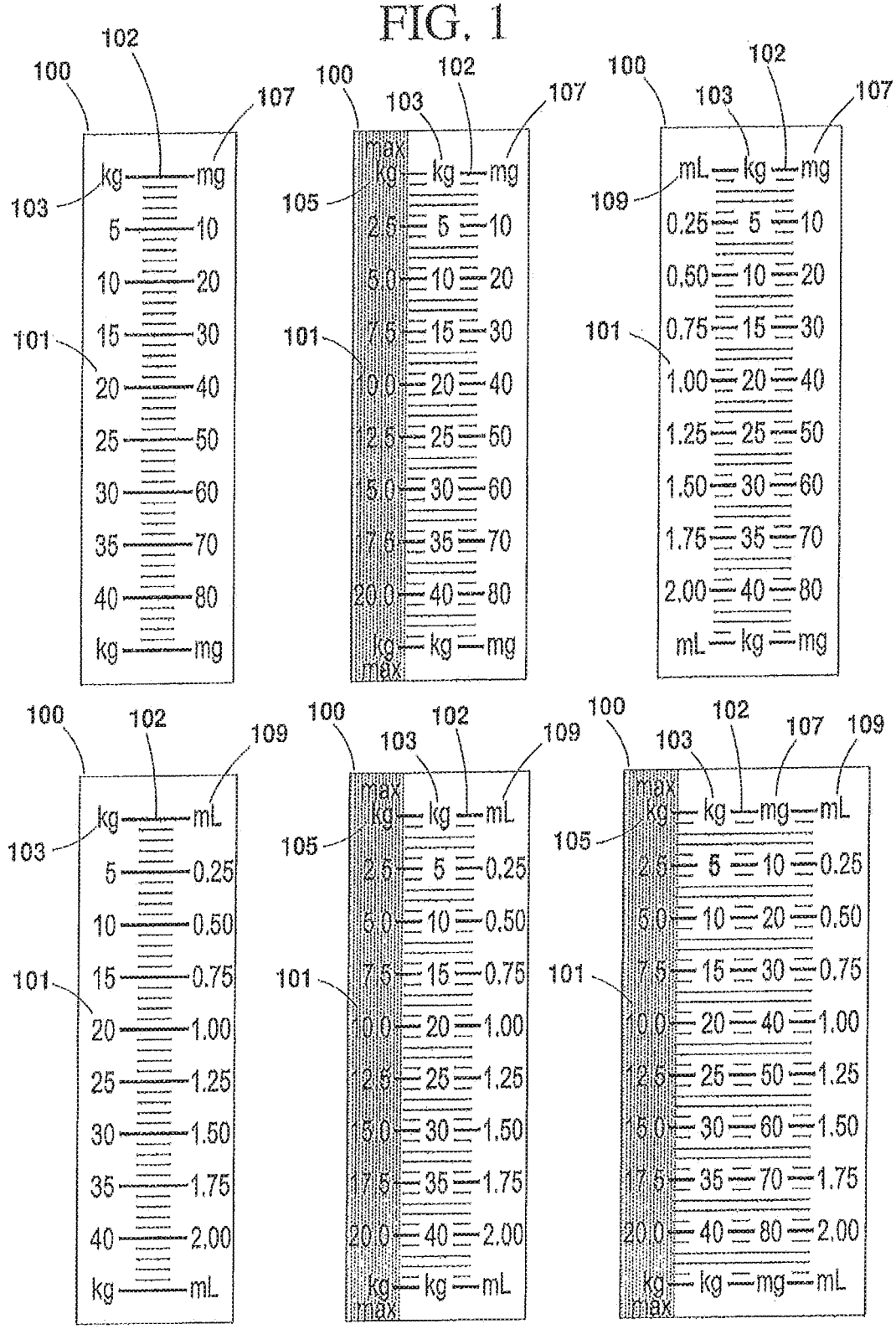
FIGS. 1, 2 and 3 illustrate close-up views of the syringe's indicia and safety re-verification indicators including indicia and indicators that appear on the syringe.
Figure 2:
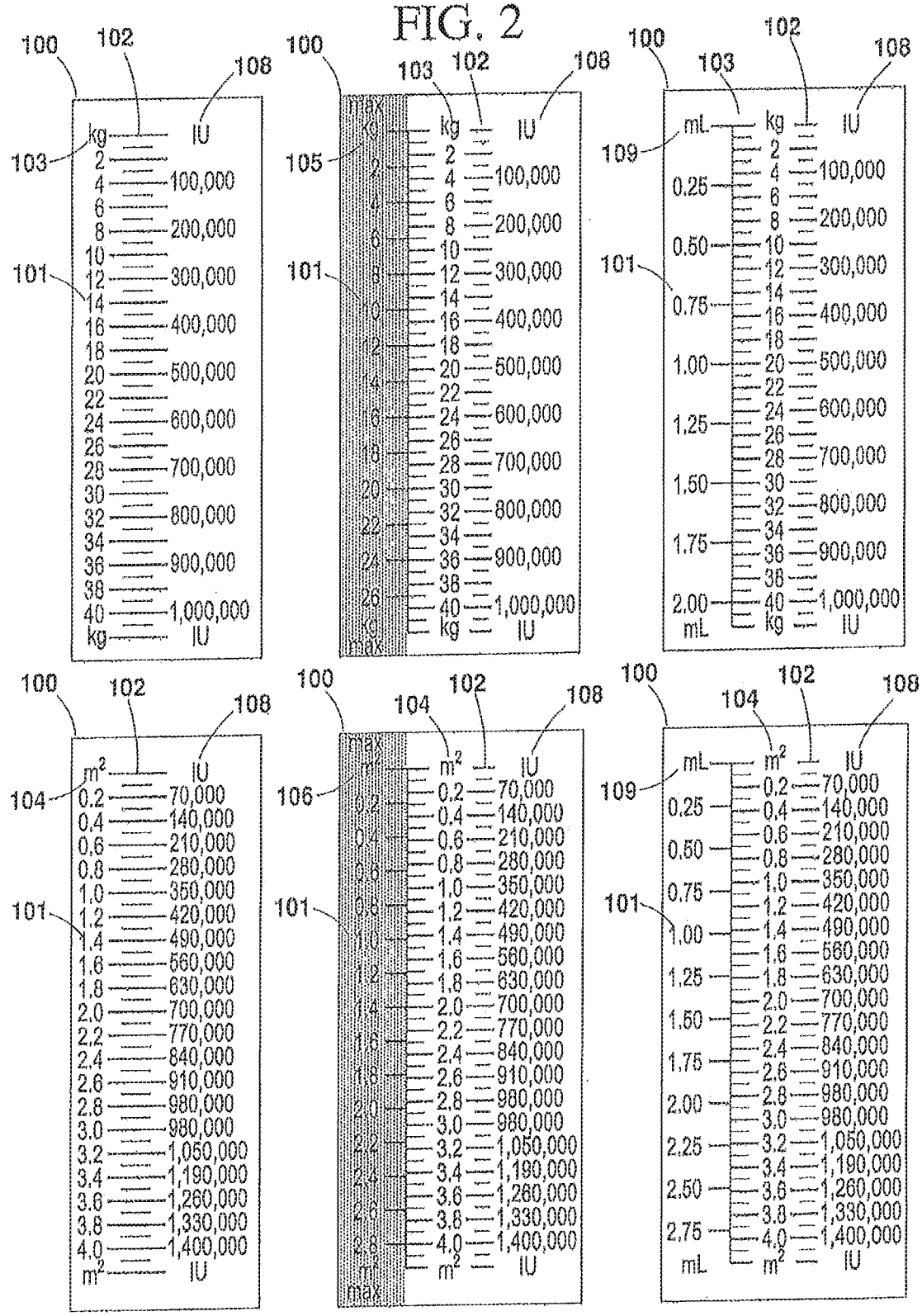
Figure 3:
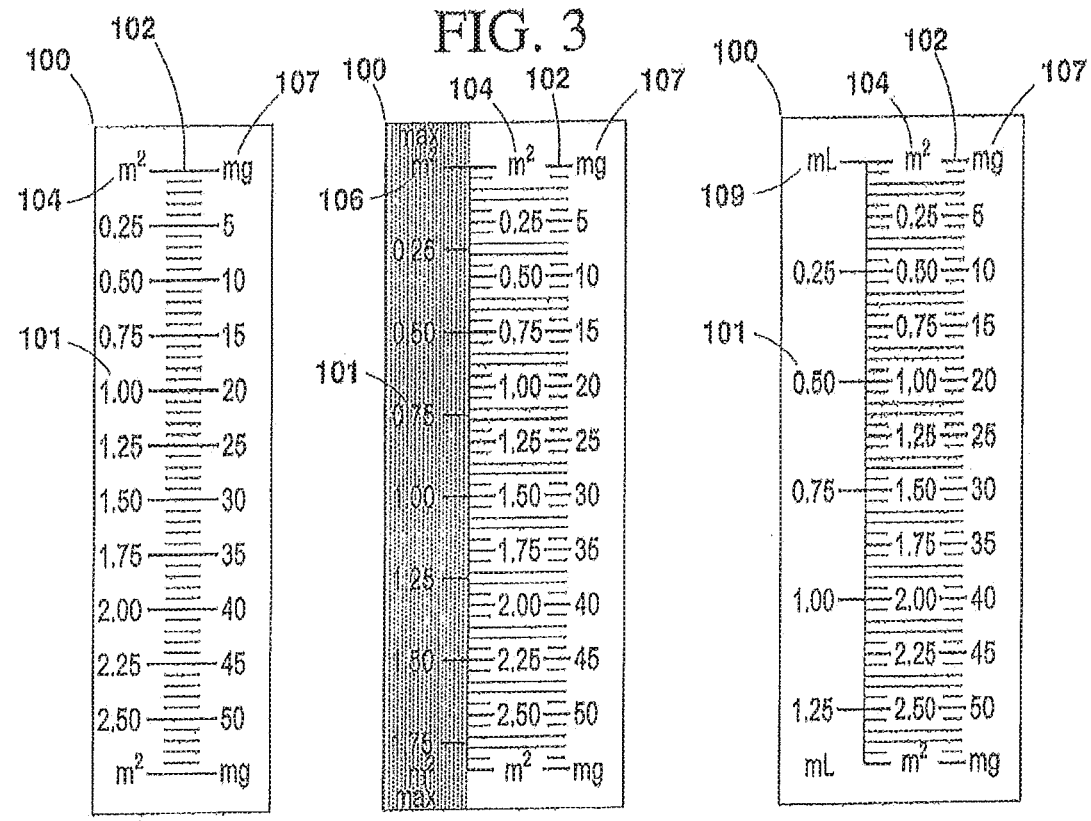
Figure 3:
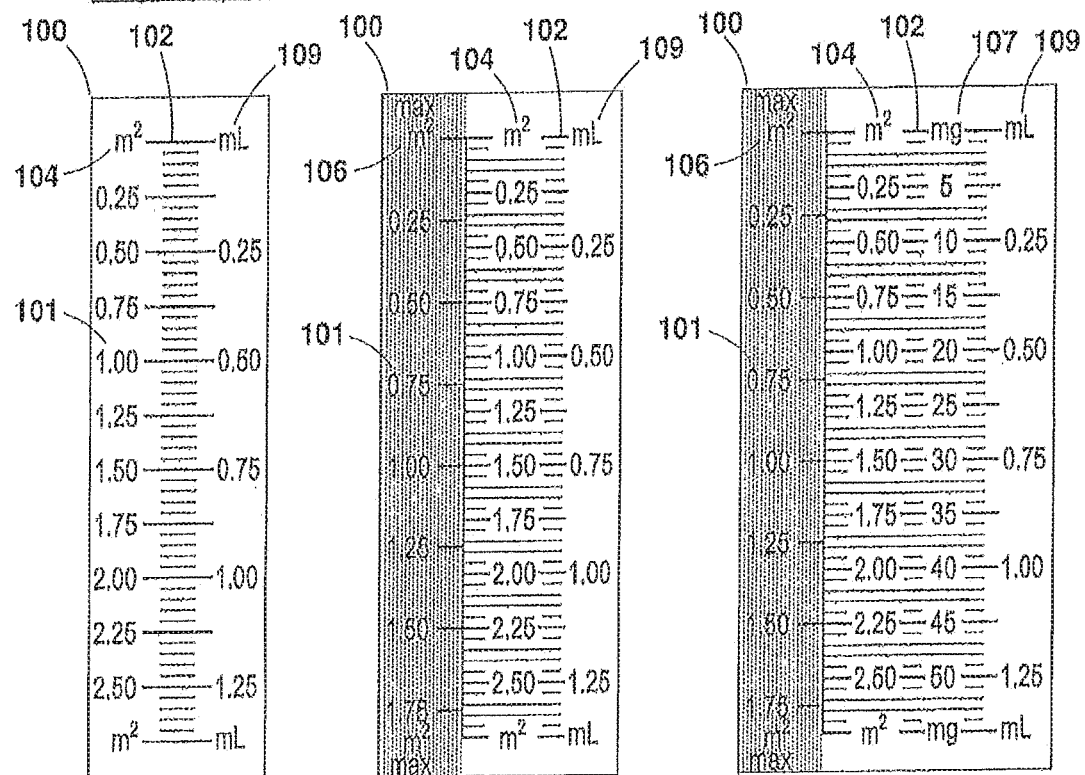

The syringe's indicia may also provide a maximum calibrated column that correlates to the maximum MCG, CC, IU, MG, ML dosage-to-patient's particular weight or BSA, (G, KG, LB, m) utilizing the recommended manufacturer's dosage schedule. FIGS. 1-3 illustrate several variations of indicia 100 for embodiments of the present invention Indicia 100 comprises measuring characteristics 101 and graduation markings 102 that correlate and correspond the patient's weight or BSA measures in KG 103, or $m^2$ 104, or LB or G to the recommended dosage for the patient's weight comprising measuring characteristics MG 107, IU 108 mL 109 or MCG. Indicia 100 may also include measuring characteristics 101 and graduation markings 102 that correlate and correspond to the recommended maximum dosage based on the patient's weight 105 or BSA 106. Indicia 100 may also include measuring characters 101 and graduation markings 102 that correspond to the strength (or concentration) 107 of the medication within the dosage. Indicia 100 may also include measuring characters 101 and graduation markings 102 that correspond to the amount of a substance 108 based on the biological activity or effect of the medication within the dosage. Indicia 100 may also comprise measuring characters 101 and graduation markings 102 that correspond to volume 109 of the medication.

Figure 4:
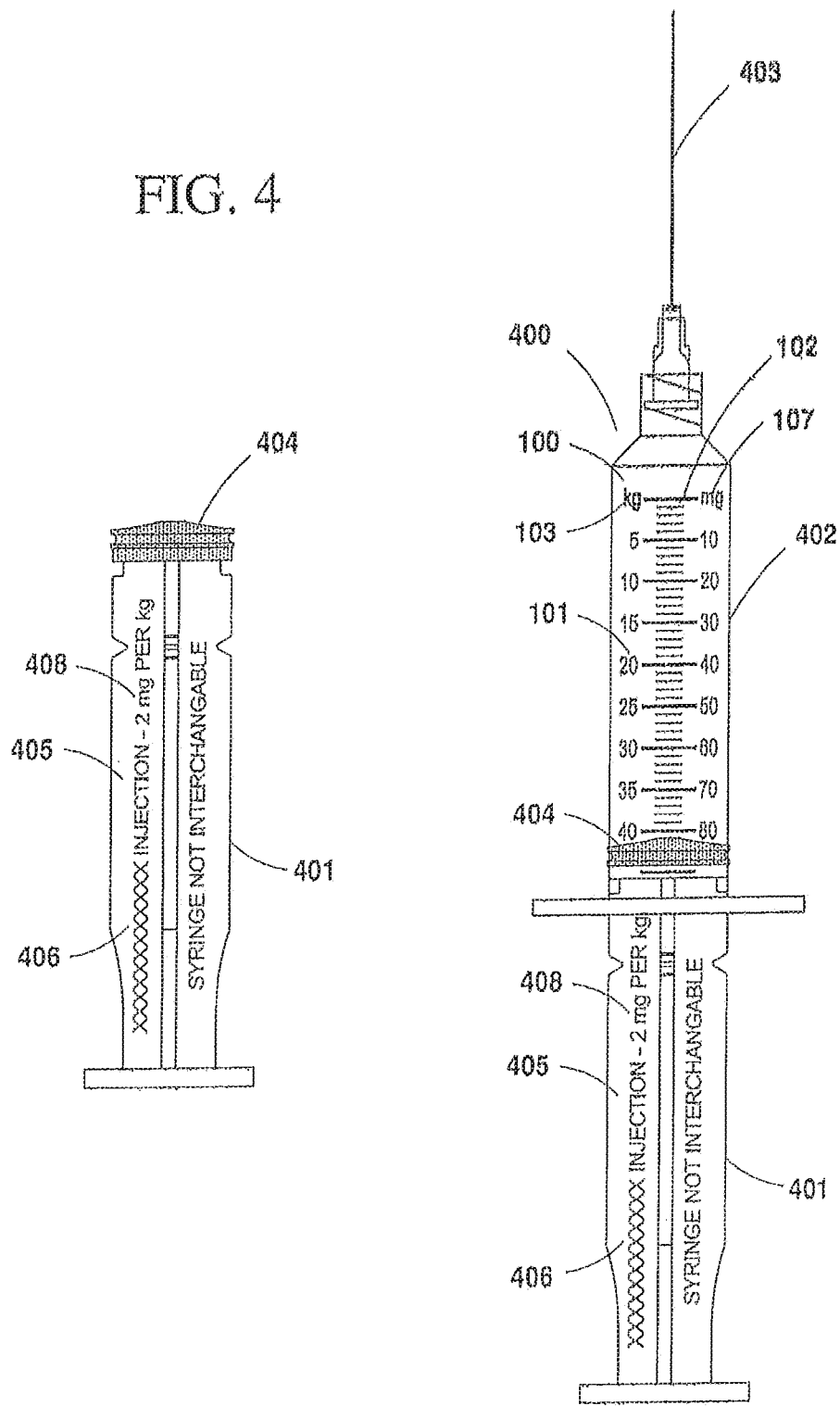
FIG. 4 is a close-up view of the plunger section of a syringe according to one embodiment of the present invention with permanent identifying destination of the medication for which it is designed and intended for, medication dosage to weight and that the syringe is not to utilized outside of the kit or with any other medication.

According to the present disclosure, FIG. 4 shows a pre-calibrated syringe 400 comprising a plunger 401, a syringe barrel 402, and a needle 403. The syringe barrel 402 comprises measuring indicia 100 corresponding to dosages based on a patient's weight 103 or body surface area (not shown). The syringe preferably comprises a gasket 404 located at and attached to one end of plunger 401. Gasket 404 is preferably made from rubber or other sterilizable material and may be modified as to be colored or exhibit fluorescent properties in natural light or upon exposure to light outside of the visible spectrum (e.g. ultraviolet light, infrared, etc.) to assist in the visible accuracy obtained in preparing and verifying the dosage per calibration scale.

Figure 5:
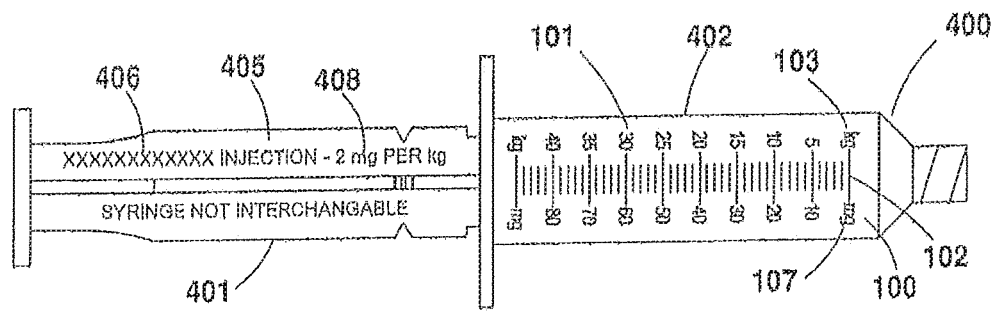
FIG. 5 illustrates the syringes according to embodiments of the present invention with various indicia and the plunger designations, including the name of the medication, dosage of the medication to the weight of the patient, and that the syringe is exclusively calibrated to that medication.
Figure 5:
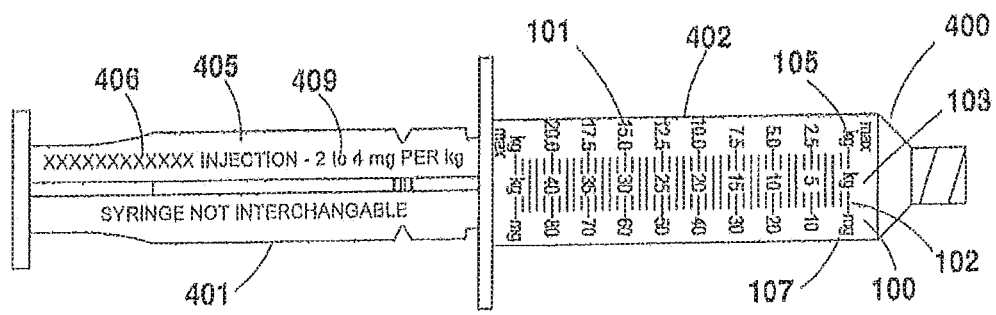
Figure 5:
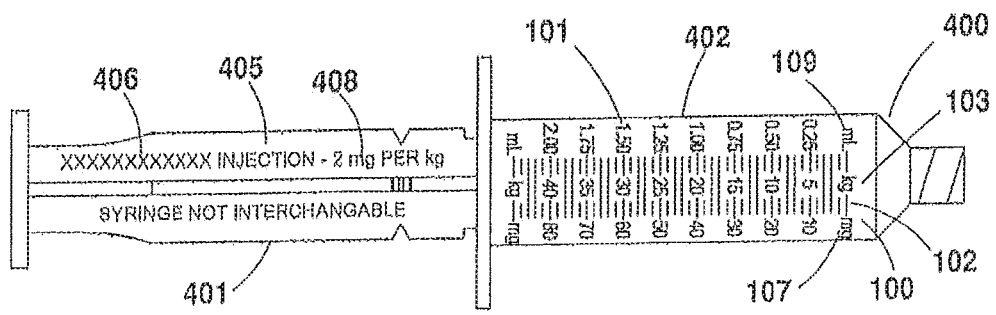
Figure 5:
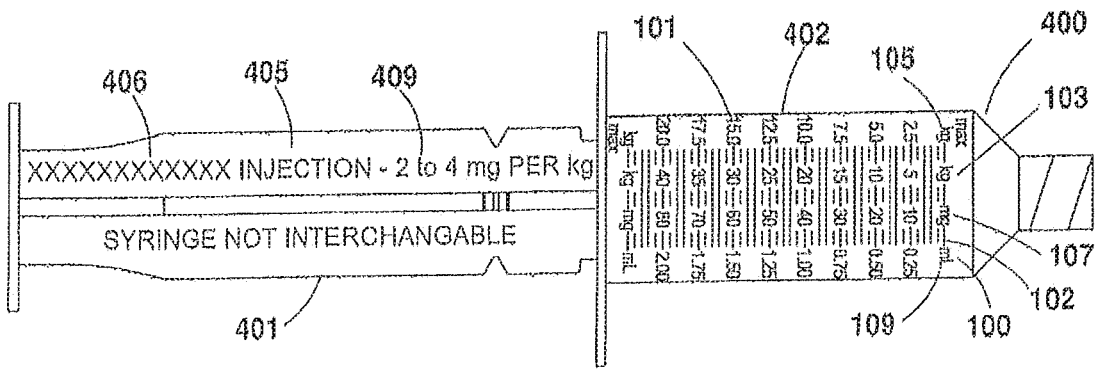

FIG. 5 shows examples of pre-calibrated syringes 400. The syringe 400 comprises a plunger 401 and a syringe barrel 402 comprising measuring indicia 100 that correlate and correspond medication dosage in MG 107, IU 108, mL 109 or MCG to an individual patient's weight 103 or body surface area (not shown) According to one embodiment, the plunger 401 preferably comprises a clear and conspicuous substantially permanent indication 405 of at least the medication name 406, dosage strength, recommended dosage to weight 408, or weight range 409 or the medication contained in the syringe. The syringe provides users with several key visual aids that help to avoid, for example, administration errors in the dosage of the medication, the use of the medication itself, the strength of the medication, etc.

Figure 6:
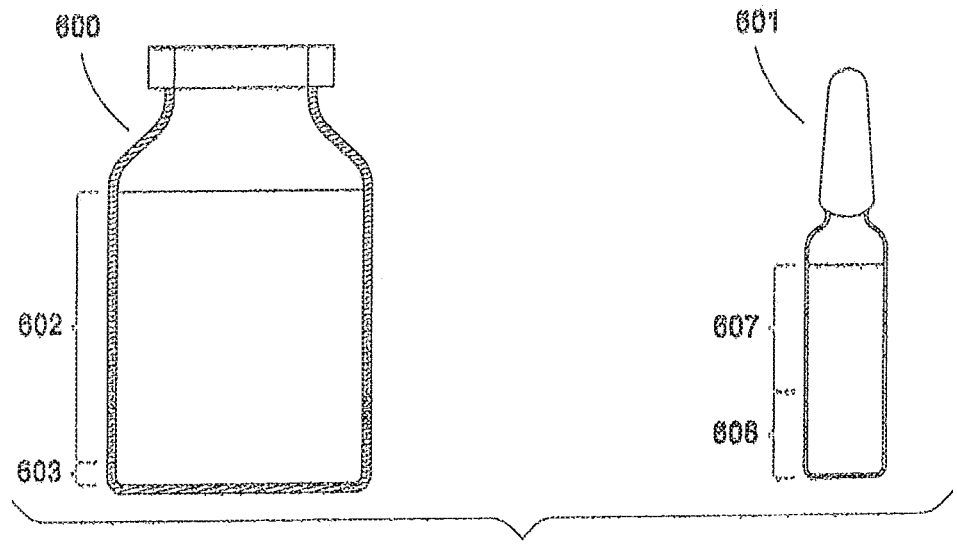
FIG. 6 illustrates an industry standard pre-filled 500 mg vial and 100 mg ampoule that would be used for the injection of 8 kg or less into a pediatric patient and the unused medication that would be wasted if a 5 mg/kg dosage were to be administered.
Figure 6A:
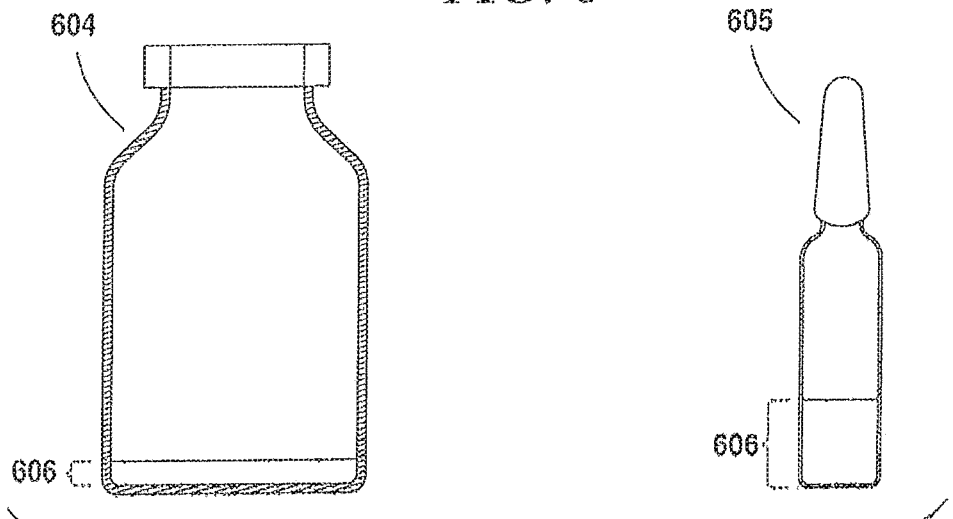
FIG. 6A illustrates a volumetrically-scaled patient weight range specific pre-filled 40 mg vial or ampoule within the combination kit that would be utilized for the injection of less than 8 kg of medication to a pediatric patient that would result in little or no waste, depending on the patient injection.

FIG. 6 shows an industry standard pre-filled (either dry or liquid) 500 mg vial 600 and 100 mg ampoule 601 of injectable medication. In this example, a low dose pediatric or reduced-weight patient dosage injection of 5 mg per kg for an 8 kg patient would require 40 mg 603 and 608. By contrast, FIG. 6A illustrates a volumetrically-scaled patient weight range pre-filled 40 mg 606 in vial 604 or ampoule 605 within the combination kit that would be used for the injection of the medication to, for example, the 8 kg or less pediatric patient that would result in a minimum 460 mg of the 500 mg vial not being wasted (the volume shown as 602) or in a minimum of 60 mg of the 100 mg ampoule not being wasted (the volume shown as 607) as would otherwise occur. (See FIG. 6).

Figure 6B:
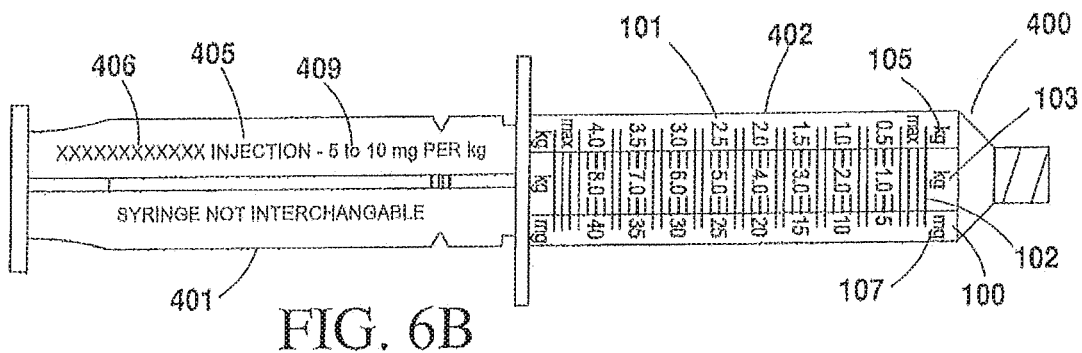
FIG. 6B illustrates a view of the syringe contained within a combination kit of calibrated for a medication strength of 5 mg/kg for pediatric range weights of 0.5 to 8.0 kg.

FIG. 6B shows a volumetrically calibrated syringe 400 to specifically correlate to the medication with the kit, and volume-scaled small dose patient range 606 to solely correlate with the vial or ampoule medication dosage strength of 5 mg/kg for pediatric range weights of from about 0.5 to about 8.0 kg.

Figure 7:
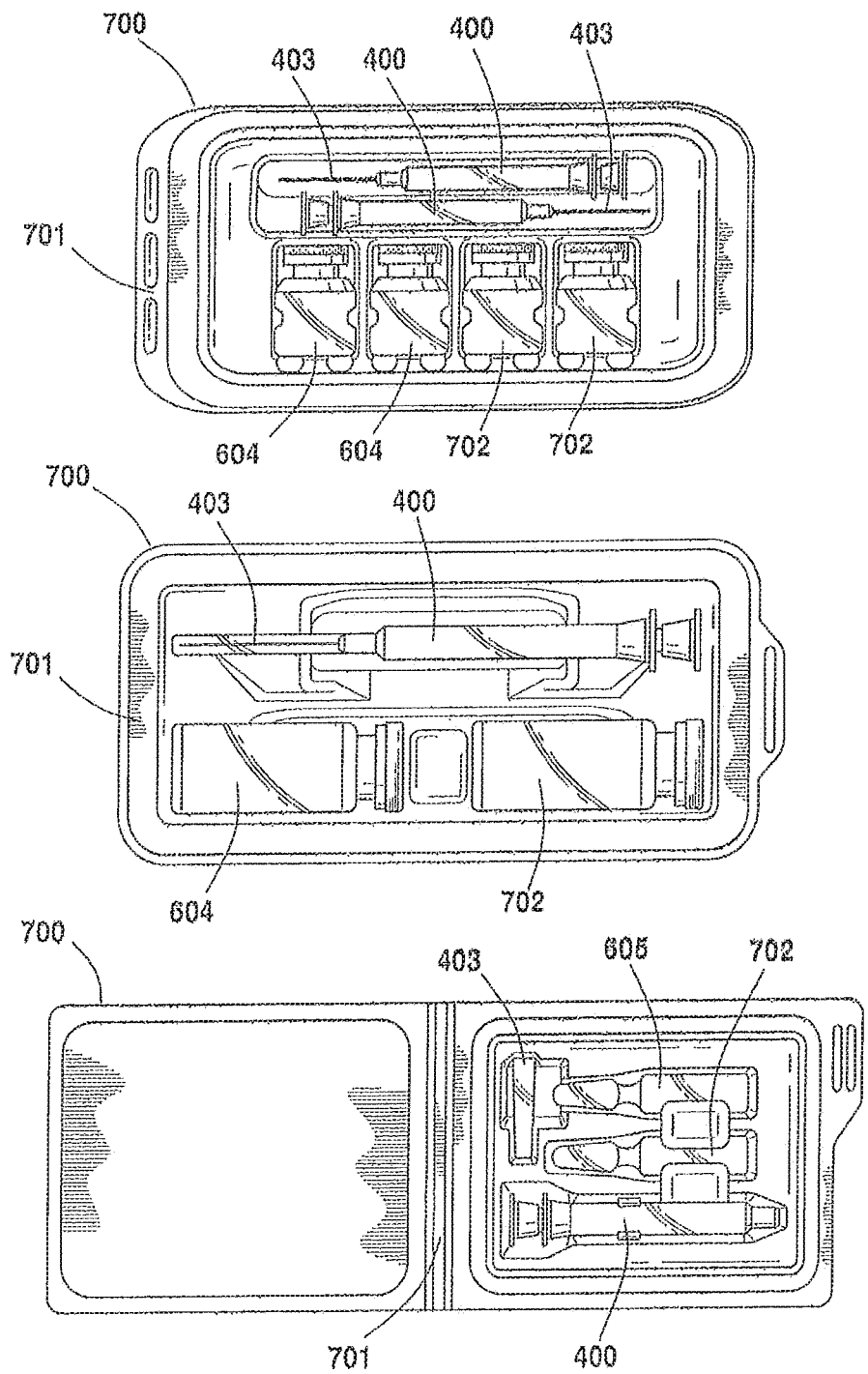
FIG. 7 illustrates views of a two syringe multi-diluent vial combination kit, where by one syringe can be calibrated and its indicia correlated specifically to the diluent(s) and the withdrawal and introduction of them into the medication for reconstitution. The other syringe is calibrated and its indicia correlated specifically for the medication and the withdrawal and administration of the dosage of the medication to individual patient weight or BSA.

FIG. 7 illustrates variations of a pre-packed kit 700 contemplated by embodiments of the present invention. The pre-packaged kits 700 consist of a single unit, preferably tamper-resistant container packaged as a "blister pack" or as a "clamshell", as would be readily understood in the packaging field. Such packaging 701 is preferably made from sterilizable materials including a plastic such as, for example, high density polyethylene (HDPE), polyethylene terephthalate (PET), polycarbonate, etc. The kit comprises pre-filled (dry or liquid) medication vials 604, or ampoules 605, corresponding diluent(s) (if applicable) 702, hypodermic needles 403, and the pre-calibrated syringes 400 for the medication contained by the kit.

Figure 8:
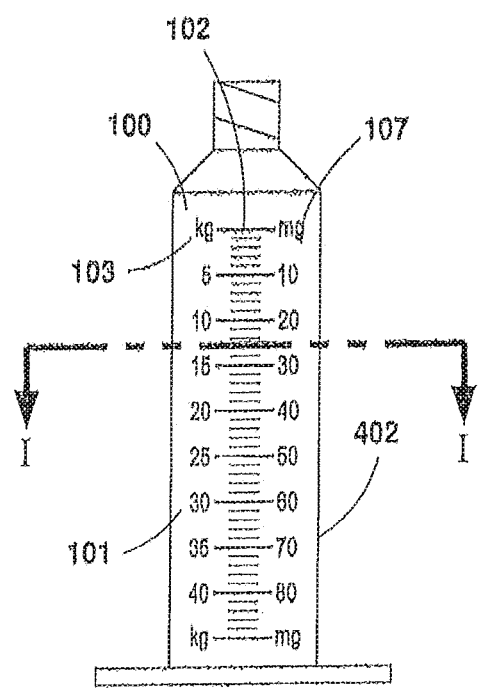
FIG. 8 illustrates a cross section of the syringe showing the exterior diameter of the barrel in various options available yet the inner barrel calibrated to individual dosage volumes.
Figure 8:
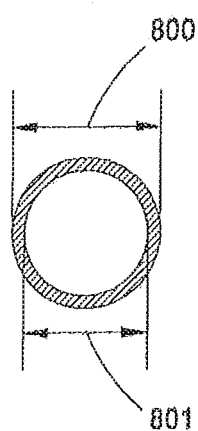

FIG. 8 illustrates a pre-calibrated syringe barrel 402 according to embodiments of the present invention. The syringe barrel comprises measuring indicia 100 that correspond to dosages based on a patient's weight 103 or BSA (not shown). Measuring indicia 100 may appear on the inner surface and/or outer surface of the barrel 401, or the barrel may be manufactured to position the indicia at a pre-selected distance located between the inner and outer surface of the barrel 402, or any combination thereof as desired. The syringe barrel 402 comprises an internal core diameter 801 and an outer diameter 800, both of which may be adjusted through desired and pre-selected design features and manufacturing. However, the outer diameter 800 may be dimensioned to be consistent with industry standard dimension, thus enabling the syringe user to have the dexterity of an accepted, larger diameter barrel syringe (such as, for the preparation and administration of medication), as well as better visibility, particularly for smaller volume injections, and visibility of the corresponding indicia.

Figure 9:
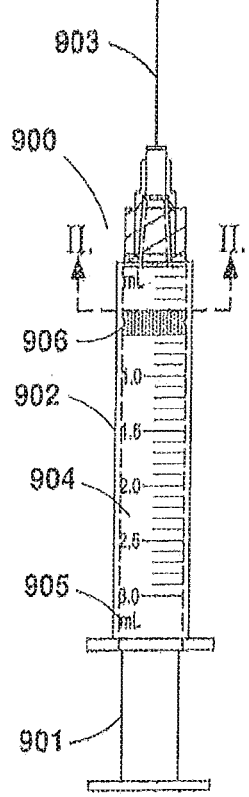
FIGS. 9-10 illustrate a typical small volume injection within a industry standard 3 ml volume syringe and the indicated level of the dosage on the indicia.
Figure 9:
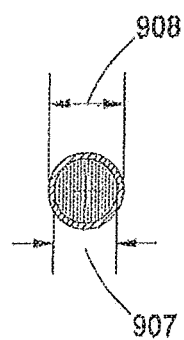

FIG. 9 illustrates an industry standard 3 ml syringe 900. The syringe 900 comprises a plunger 901, a syringe barrel 902, and a needle 903, or sharp. Measuring indicia 904 may appear on the inner surface, outer surface of the barrel 902, or the barrel may be manufactured to position the indicia at a pre-selected distance located between the inner and outer surface of the barrel 902, or on any combination of surfaces thereof. The measuring indicia preferably correspond to the volume 905 of the syringe Plunger 901 comprises a gasket 906 at one end of plunger 901. The gasket 906 is preferably a rubber piston gasket that indicates the volume within the syringe barrel 902. The internal diameter 907 and the outer diameter 908 of the syringe barrel 902 may be manufactured to industry standard sizes.

Figure 10:
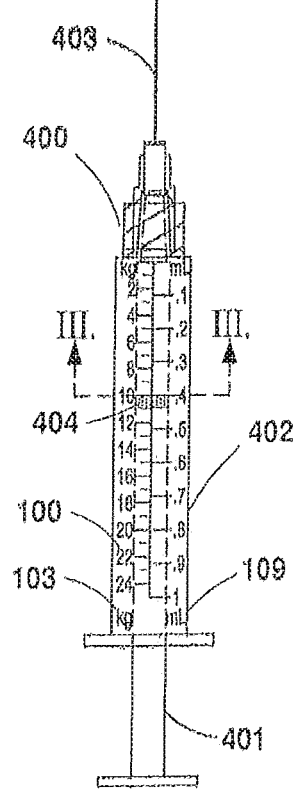
Figure 10:
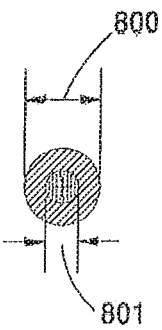

FIG. 10 shows a pre-calibrated syringe 400 according to embodiments of the present invention. Syringe 400 comprises a plunger 401, a syringe barrel 402 and a needle 403. Syringe barrel 402 comprises measuring indicia 100 that may appear on the inner surface, outer surface of the barrel 402, or the barrel may be manufactured to position the indicia at a pre-selected distance located between the inner and outer surface of the barrel 402, or on any combination of surfaces thereof. Plunger 401 comprises a gasket 404 at one end of plunger 401. The gasket 404 is preferably a rubber piston gasket that indicates the volume within the syringe barrel 402. The internal, or core diameter 801 and the outer diameter 800 of the syringe barrel 402, both may be adjusted though desired and pre-selected design features and manufacturing. However, the outer diameter 800 may be dimensioned to be consistent with industry standard dimension, thus enabling the syringe user to have the dexterity of an accepted, larger diameter barrel syringe (such as, for the preparation and administration of medication) as well as better visibility, particularly for smaller volume injections, and visibility of the corresponding indicia.

The syringe may be volumetrically calibrated and its indicia adjusted for the dosage strength of the particular medication that is appropriate for a patient in a specific weight range, m², or dosage range. This allows clearer and more gradient-correlated dosage-to-weight or BSA (m²) calibrated indicia for precise dosages than standard non-calibrated industry syringes (See FIG. 9). This feature permits volumes to be calibrated and measured in a smaller, more precise, gradient indicia scale for lower incremental doses, such as dosages for infants, pediatric patients, and other patients who are unusually sensitive to the medication as well as for the injection of extremely potent and dangerous medications such as pain management, anesthetics, biologics and oncology drugs than standard non-calibrated industry syringes (See FIG. 10).

The syringe may also offer a fluorescent (or other colored) rubber piston gasket at the plunger tip, whereby maximum visual accuracy is obtained in preparing and verifying the dosage per calibration scale. (See FIG. 4, feature 404).

Further embodiments of the present invention allow the user to see the dosage of the subject medication in a singular calibrated measurement indicia that specifically correlates to another calibrated measurement indicia corresponding to the patient's weight or other characteristic(s), etc. (See FIGS. 1-3).

Further embodiments of the present invention also offer a calibrated measurement indicia for a manufacturer's maximum suggested dosage of a subject medication that also specifically correlates to another calibrated measurement indicia corresponding to the patient's weight or other characteristic(s). (See FIGS. 1-3).

In further embodiments, the syringes of the present invention may also bear additional separate pre-calculated measurement indicia specifically designed for a subject medication that enables the user to verify that he or she is administering the correct dosage (See FIGS. 1-3).

The present invention substantially eliminates risk of human error associated with computations ordinarily conducted by healthcare professionals relative to performing dosage-to-patient weight or BSA calculations, provided the user follows the pre-calibrated indicia on the syringe. This, in turn, eliminates the primary cause of Medical Administered Errors (MAE) for injected medications.

The pre-packaged combinatorial kit of the present disclosure containing a reconstitutable medication, the corresponding diluent(s), and the pre-calibrated syringe(s) for the medication and diluent(s) within the kit, substantially eliminates multiple methods and procedures that are the leading direct cause of MAE from an injectable administration. The combination kit substantially completely eliminates vital user procedures and methods ordinarily conducted by healthcare professionals, specifically: the collection of the correct medication for patient and patient class, the correct corresponding diluent(s) for particular medication, the correct diluent(s), syringe and needle for the particular route of administration, the correct calculation, measurement and procedures for the correct reconstitution of the medication by the diluent(s), the calculation determination of dosage-to-patient weight or BSA, and the subsequent verification of these procedures prior to the injection. The removal of these procedures and methods substantially eliminates the risk of human error associated with them. This, in turn, substantially eliminates the primary causes of Medical Administered Errors ("MAE") for injected medications. (See FIG. 7). The pre-packaged combinatorial kit of the present disclosure containing a medication in solution form, and the pre-calibrated correlating syringe(s) for the medication within the kit, substantially eliminates multiple methods and procedures that are the leading direct cause of MAE from an injectable administration. The combination kit substantially completely eliminates vital user procedures and methods ordinarily conducted by healthcare professionals, specifically: the collection of the correct medication for patient class, the syringe and needle for the particular route of administration, and the calculation determination of dosage-to-patient weight or BSA, and the subsequent verification of these procedures prior to the injection. The removal of these procedures and methods substantially eliminates the risk of human error associated with them. This, in turn, substantially eliminates the primary cause of Medical Administered Errors ("MAE") for injected medications. (See FIG. 7).

In a further embodiment of the present disclosure, the pre-packaged combinatorial kit containing a reconstitutable medication, the corresponding diluent(s) for the reconstitution(s), and the pre-calibrated syringe for the medication within the kit may yet further eliminate additional industry standard procedural user steps and methods including: research, calculations, measurements and verifications for the correct volume of diluent(s) necessary for the correct reconstitution(s) of the medication within the vial. The diluent(s) within the kit is volumetrically specifically calibrated to offer the correct dilution of the medication within the kit. The user needs only to withdraw the diluent completely from the vial or ampoule and then to completely inject that volume into the vial of the medication, thus eliminates multiple methods and procedures that are direct causes of MAE from an injectable administration.

In a further embodiment of the present disclosure, the pre-packaged combinatorial kit containing a reconstitutable medication may also have a calibrated syringe for the diluents(s) within the kit that would provide specific indicia to provide the proper withdrawal of the diluent into the diluent syringe for the subsequent correct procedures and methods for the reconstitution of the medication within the kit.

In a further embodiment of the present disclosure, the pre-packaged combinatorial kit may contain one of more syringes or needles for the syringes Embodiments of the present disclosure substantially reduce the cost associated with having healthcare providers prepare, collect, and correlate the correct components for the medicinal injection for a particular patient because the present invention eliminates the need for a healthcare provider to perform these functions and the need for the calculation to then be verified, and the administration authorized, by a supervisor or other healthcare provider.

Variations of the present disclosure may substantially reduce a heath care institution's liability insurance costs by reducing and/or eliminating MAE that result from the injection of medications and also by implementing a more sophisticated passive safety system, and methods and apparatus than typical industry standard practices.

According to embodiments of the present disclosure, the incorporated measurement indicia on the syringe offers crucial double or triple visual re-confirmations, including, for example, dosage to patient weight or BSA, name of medication, recommended dosage to weight and/or maximum dosage per weight, allowing the user to perform last-minute safety checks, and thereby discontinue or revise the dosage while preparing or even administering the medication. These enhanced visual aids further prevent incorrect or over-dosage of the patient even at the last stages of the administration. (See FIGS. 1-6).

According to further embodiments of the present disclosure, the internal core diameter of the syringe barrel may be reduced to enable holding smaller volumes of the medication in a thinner barrel (a barrel having a reduced diameter), thereby making the measurement indicia more precise. A smaller core diameter makes it possible for the medication to be further disbursed in the syringe barrel, thus effectively extending the volume of the medication further into the syringe barrel. The calibrated volume in the barrel enables the dosage-to-patient-weight-calibrated measurement indicia to be visually enhanced by expanding the measurement indicia into a larger elongated scale and thus also offering more precise and lower graduated measurement increments. This visual enhancement will also help ensure the administration accuracy for smaller, more precise doses, such as, for example, doses for pediatric patients, etc. (See FIGS. 9 and 10).

In still further embodiments of the present disclosure, the internal core diameter of the syringe barrel may be adjusted by through various design features, yet the exterior diameter of the syringe barrel may not be adjusted, enabling the user to have the dexterity and/or better visibility of a larger diameter barrel syringe for the preparation and administration (See FIGS. 8 and 9).

Another embodiment of the disclosure is directed to a vial or ampoule or other container containing a pre-determined volumetric measurement of a specific medication that would specifically correlate to the dosage-to-weight or dosage-to-BSA calibrated measurement indicia on the syringe. This pre-determined amount could then be loaded into the syringe at the time the medication is administered to the patient. Accordingly, in this embodiment, there would be no calculations or correlations necessary for the user to load the syringe from the vial or ampoule or other container to the correct dosage of the medication to the patient's weight for administration.

Additional embodiments contemplate allowing the dosage to patient weight calibrated measurement indicia on the syringe to uniquely target specific weight scales, customized for adult, pediatric, or infant weight, etc. The calibrated measurement indicia scale would thereby allow better visibility as it is specifically focused on a particular weight and patient range allowing for more accurate incremental dosages and less over all waste through this volume-scaled patient range calibration. (See FIG. 6).

Embodiments of the present disclosure consist of a single-use syringe that is pre-filled at the time of manufacture with a pre-determined volume of a particular medication. The specific dosage of the subject medication could then be administered according to the syringe's calibrated measurement indicia that is pre-calculated based on the weight of the patient or BSA and the correlating dosage. It further allows the user to see the dosage of the subject medication in one calibrated measurement indicia that specifically correlates to another calibrated measurement indicia corresponding to the patient's weight or BSA In another variation, the syringe may come in a combination kit containing a separate pre-filled (either dry or liquid) vial or ampoule injectable medication that is specifically volume-scaled to solely correlate with the syringe's volumetric design and calibrated measurement indicia. (See FIG. 6). In this case, the syringe could be loaded and administered without the need for any calculations of the subject medication to patient weight. The syringe would also be a "ready-to-fill" syringe that would have various preselected indicia stamped on it including, for example, the name of medication, strength of medication and the dosage strength-to-patient weight, etc. (See FIGS. 4-7).

In another embodiment, the syringe may come in a combination kit containing a separate pre-filled dry vial injectable medication with a corresponding vial or ampoule of diluent for reconstitution of the dry vial injectable medication into a solution. Both the dry powder vial of the injectable medication and the corresponding diluent are also specifically volume-scaled to solely correlate each other with the syringe's volumetric design and calibrated measurement indicia. In this embodiment, the diluent would be completely extracted by the syringe from the diluent vial or ampoule, thereby eliminating the need for measurement or calculation and then completely injected into the dry powder vial of the injectable medication for the reconstitution of the powder into a solution. The injectable medication then is extracted out of the vial with the syringe according to the proper weight indicia on the syringe, and then medication is administered to the patient. All of these steps substantially eliminate the need for calculations or correlations of the medication's reconstitution and the calculation of the subject medication to patient weight based upon the unique pre-calibration and correlation of the invention itself. (See FIG. 7).

In another embodiment, the syringe plunger in both versions, pre-filled and ready to fill, may be substantially permanently stamped with one or more identifying designations including, for example, name of the medication that it contains, the strength of the medication that it contains, and the dosage-to-weight correlation for the patient for whom it is intended, etc., thereby helping to prevent the administration of the wrong medication and/or wrong dosage strength of the medication to the patient. Known syringes do not bear this information. (See FIGS. 4-5).

There are no known syringes that combine all of these safety aspects that enable the user to verify that he or she is using the appropriate syringe for the patient in question. The present invention's calibrated measurement indicia that appear on the syringe barrel are individually correlated to the specific medication and the manufacturer's recommended dosage amount for the patient's specific weight. The present disclosure's syringe indicia therefore addresses and prevents two of the most common MAE's plaguing the health care industry, namely: 1) wrong dosage, and 2) wrong medication.

In addition, embodiments of the present disclosure eliminate the need for a user to calculate the dosage strength of medication (mcg, cc, iu, mg, ml) to corresponding patient weight or BSA (G, KG, LB, $m^2$). The re-verification safety check calibration indicia that appear on the syringe provide users with several key visual aids to avoid, for example, administration errors in the dosage of the medication, the medication itself and the strength of the medication, etc. (See FIG. 5).

In one embodiment, the syringe plunger comprises a clear and conspicuous substantially permanent indication of at least the medication name, dosage strength and recommended dosage to weight of the medication that it contains. (See FIGS. 4 and 5). The preferred syringe's safety re-verification indicators within the calibration measurement indicia offer a clear indication of dosage in a column dedicated to MCG, CC, IU. MG, ML, and then substantially simultaneously further offers a clear conversion of the correlating figure in a G, KG, LB, utilizing the recommended manufacturer's dosage schedule in another parallel column (See FIGS. 1-3).

Presently known syringes and kits for administering injectable medication offer few or no safety checks. In strong contrast, the embodiments of the present invention substantially minimize the risk of human error in the administration of injectable medication to a greater degree than any other design presently known. The user does not have to calculate the appropriate dosage for the individual patient weight to load the syringe from a vial or ampoule or administer the medication. The user must simply follow the syringe's indicia and load and inject, or in the case of a pre-filled syringe, inject the medication according to the designed patient weight indicia.

Unlike all known medication administration systems, embodiments of the present disclosure may be used for all drug applications, dry fill vial, lyophilized vial, liquid vial, ampoule, and prefilled injection, without a variation in any way from the original manufacturer-indicated administration of the injectable medication or the manufacturer's original regulatory stability approved packaging.

Unlike known medication administration systems, embodiments of the present disclosure substantially eliminate the need for complicated color coding, additional containers, calibration, conversion, additional equipment, drug components, further calculations, open or reusable drug products, cleaning and sterilization of any equipment or components, etc. This is because the alternatives of the present disclosure bear indicia that are pre-calibrated to the specific medication for which it is intended. The user is therefore not required to perform any further calibrations or calculations.

Further, unlike known products and methods, the present variations will not require that users undergo any complicated education and/or training. Embodiments of the present disclosure offers health professionals, multiple, clear and available visual verification features and re-verification features to prevent MAE's that other syringes and devices currently on the market lack.

According to present embodiments, a syringe, in both pre-filled and ready-to-fill versions, will be permanently stamped with the name of the medication, dosage strength of medication and recommended dose-to-weight on the plunger, thereby helping to prevent the administration of the wrong medication and/or wrong dosage strength of the medication to the patient. Known syringes do not bear this information.

According to further embodiments of the present invention, a syringe in both pre-filled and ready versions will permanently bear the dosage strength of the medication contained therein on the plunger. See FIG. 4. This will further prevent users from administering the wrong dosage of the medication. Known syringes do not bear this conspicuous information on the plunger.

Further embodiments of the present disclosure contemplate a system, kit and syringe with its calibrated measurement indicia and volumetric design comprising a pre-determined, pre-filled volume of the medicine pre-calculated and specifically correlated from the volume strength (MCG, MG, ML, IU, CC) to the patient weight or BSA (G, KG, LB, $m^2$) based on the particular manufacturer's suggested drug product dosage schedule. The user does not need to perform any calculations to determine the proper dosage. The user must merely know the weight or BSA of the patient and then use the syringe designed for a patient of such weight range. All calculations and correlations of volume (MCG, MG, ML, IU, CC, $m^2$) are pre-converted and appear in a corresponding column for the particular injection into measures of the weight or BSA of the patient (G, KG, LB, $m^2$), corresponding with that particular manufacturer's injectable drug product dosage schedule. (See FIGS. 1-3).

Pharmaceutical manufacturers may produce the syringes, according to embodiments of the present disclosure, that are intended for a specific targeted patient group by volumetric adjusting the syringe's volume capacity and the calibrated measurement indicia to a targeted patient weight group. In the case of pediatric or infant injectables, a major issue stems from a typical volume syringe with a large calibration scale for adults. In most cases, it is much more difficult to accurately prepare smaller doses than if the volume and the syringe was downsized and thus the scale specifically pre-adjusted to that particular patient weight scale (0.5 KG to 10.0 KG in MCG or MG, etc.). (See FIGS. 6-10).

Preferably, the barrel of the syringe may offer two or three or more calibrated measurement indicia. In one column the medication contained therein will be measured by volume dosage (MCG, MG, CC, ML, IU strength). In the second column, for example, a direct correlation to corresponding patient weight or BSA (G, KG, LB or $m^2$) based upon the manufacturers recommended dosage. The barrel of the syringe may offer a third calibrated measurement indicia column providing yet another correlation in grams, kilograms, pounds or m² that would indicate the maximum dosage schedule for that patient weight or BSA. Preferably, either or all three columns in the calibration scale on the syringe could be clear or color tinted (for example, yellow for recommended dose and red for maximum dose, etc.). (See FIGS. 1-3).

Still further, according to an embodiment of the present disclosure, the syringe may be pre-filled ready for injection or within a pre-determined kit containing volumetrically pre-calibrated vials or ampoules which would require no calculations or correlations for the subject medication dosage amount verses weight of patient. This substantially eliminates the risk of human error inherent in known systems, methods and apparatuses. The downsizing of a single dose vial or ampoule to an individual kit for pediatric, creates a cost savings by avoiding the tremendous waste associated with discarding the unused remainder of a vial or ampoule of medication that occurs when known syringes are used for reduced dosages. The re-use of single use vials is a major health contamination problem in the health care industry worldwide today. The downsizing of a single dose vial or ampoule to an individual kit for pediatric or other reduced volume dosage reduces the possibility of re-use of a single use vial based upon the end user not wanting to through away such an excess volume of the product. The reduced dosage also could limit the severity of an over dosage based upon the reduced medication volumes. (See FIGS. 6-7).

The combination kit of the embodiments of the present disclosure preferably comprise a calibrated vial or ampoule of medication with a pre-calibrated syringe with corresponding calibrated diluent(s), (if applicable, antiseptic wipes) and is preferably packaged as a single unit in a tamper resistant package and may also comprise an instructional pamphlet for the particular administration of medication, thus consolidating all the necessary components for the injection in one combination kit. No known syringe or means for administering injectable medication offers the level of safety and simplicity that the present invention provides. (See FIG. 7).

Embodiments of the present disclosure would not need additional components, combinations of components, equipment, precautionary methods, product education, instruction, sterilization, cleaning, replacement parts, nor additional stability or regulatory approvals, as are required for known devices deemed to aid and prevent MAE. Further, the present disclosure would not need a complex color coding which would require education of staff, complex procedures, additional human calculation, combinatory methods, etc. that would increase the likelihood of human error and, in the end, result in increased MAE.

Embodiments of the present disclosure would not rely on a safety platform based upon a printed sticker or a handwritten sticker or other mark or calibration that would be placed on the syringe or other apparatus to supply the necessary data for name, strength and dosage or other necessary information for the drug to be administered correctly. These features are necessary under presently known regimens Placement of a sticker, mark calculation, or other mechanism or device indicating this data relies on human calculation and combinatory methods, as well the accuracy of the medical professional placing the data sticker on the syringe and the correct syringe. Regardless of the accuracy of the sticker and it being correctly applied; (to the correct syringe, with the correct name, with the correct dosage, for the correct patient) the placement of a sticker or other type of placard still does prevent an MAE based on one of the most common MAE; an overdose or under dose of the drug due to improper calculation or misreading the calibration scale of the syringe when it is being administered by a health care professional.

Some known devices seek to create a system under which multiple drugs could be injected through a single syringe with a standard, "one fits all" calibration in multiple weights, height, age, etc. The non-drug specific syringe with these pre-determined calibrations is then placed in multi-drug containment systems that will "store" the drug products until syringe distribution. These containment systems would allow the syringe to withdraw the drug product to the pre-calibrated measurements on the syringe for the syringe then to be readied for injection. This creates a substantial risk of human error. It also requires that the medication be opened and drawn into the syringe, then injected out of its regulatory manufacturers' approved packaging only to be re-loaded and then injected into the patient, adding multiple human (relied upon) steps, and actually increasing the likelihood of a MAE. Furthermore, the known administration systems often deviate from the manufacturer's recommended administration of the drug, and industry regulations regarding removing pharmaceutical product, especially a pyrogen free injectable, out of its regulated intended packaging. Indeed, such injectables should not be held in any other packaging other than the manufacturer's original packaging. Only the manufacturer's packaging has undergone stability studies specifically for those finished dosage formulations and received medical device approvals for the distribution of the individual medicines it deems to handle. Certainly this poses a tremendous regulatory and financial burden to incorporate each and every drug product through such a process, while not solving the underlying problems posed by the increased likelihood of MAE. Many vials and ampoules are filled with nitrogen blanketing. Once open, they should not be stored and must be injected. The majority of vials are powdered and then are reconstituted to a solution for injection as a single dose and are made for immediate injection.

Many injectable medications, including oncology medications, are highly toxic or cytotoxic. It is crucial that they be exposed only in a controlled environment. If they are removed from their approved packaging, exposed to open air, and aerosolized, they can be extremely hazardous to the healthcare providers who are handling them.

In addition, any additional containers or containment systems would need to be tested for endo-toxin levels to ensure sterility or be disposed of after each use prior to being refilled. Clearly, known syringes with containment devices do not eliminate risk of MAEs by because they do not reduce the potential for human error. Instead, they increase the likelihood of MAE by increasing the need for multiple hands-on methods, procedures, steps and storage.

Furthermore the methods and practices associated with both prior arts would require changes to: health regulations worldwide, manufacturer's best mode standards for methods of administration, as well require substantial user education for these non-practiced industry procedures and activities for the medicinal administration under these scenarios.

Examples of Cost Efficiency of Present Invention Safety Convenience Kit, Vial and/or Ampoule Embodiments of the present invention allow for the scaled volume individualization of vials and ampoules that can are used with the present invention. In known practices, a typical single use vial may be in a 500 Mg vial, or a 100 Mg Ampoule (See FIG. 6, feature 601). Further to that example, a specific pediatric dosage for that drug is 5 mg/Kg. This would result in a typical pediatric patient weighing less than 40 kg (approximately 88 pounds) to require a dosage (according to recommended dosage schedule) of less than 200 mg. As a result, over half of the vial will be discarded and wasted, (this at the maximum patient body weight of 40 kg, all weights under 40 kg would only increase the waste). (See FIGS. 6 and 6A).

This is the common practice when it comes to small dosage requirements, because in the current market there are virtually no products that are specifically downsized for pediatric dosages. According to embodiments of the present disclosure, one is able to downsize the vial or ampoule (and syringe by reducing the barrel diameter) to a specific volume size, thereby enabling a specific dosage range for the intended patient application. Using the variations and alternatives in the present disclosure, one could design a convenience product wherein the drug could be scaled to an individually targeted weight class For example, a pediatric dosage can be scaled for 0.5 kg to 8.0 kg (FIG. 6A, feature 606). In this example, over 460 mgs of a 500 mg vial and 60 mg of a 100 mg vial would be wasted with current injection technology. There would be no waste using the present invention. The syringe calibration indicia of the present invention could also be enlarged to effectively offer better visibility and more precise incremental indicia. (for example in MCG). This is made possible by the volumetric pre-designed aspects of the present invention and product downsizing correlating to the present disclosure.

Examples of Cost Efficiency of Present Invention

Embodiments of the present disclosure also allow for the scaled volume individualization of pre-filled syringes. In ordinary practices, a leading typical single use pre-filled syringe (PFS) for a popular anesthetic is, for example, in a 50 mg PFS which would be used for the initial (loading) dosage at a rate of 0.5-1 mg/Kg. Therefore a 50 mg, prefilled syringe would offer enough product suitable or a dosage for a patient of up to 50 kg (110 lb) or to 100 kg (220 lb). This is the minimum size available.

According to embodiments of the present invention, one could design a product where the drug could be volumetrically scaled to an individually targeted weight class. For example, a pediatric device could be scaled for 1 kg to 20 kg in a 20 mg embodiment of the present invention. In this example, over half of the PFS would not be wasted, and, in the event of an overdose, the reduced scaled volume of the drug could also decrease the size of the overdose and, as a result, the severity of the MAE and adverse event. In this example, the syringe calibration indicia also could be enlarged to effectively offer better visibility and more precise indicia, (for example in MCG), by the volumetric pre-designed aspects of the syringe and product downsizing for the syringe.

Many modifications, variations, and other embodiments of the present invention will come to the mind of one skilled in the field to which this invention pertains, having the benefit of the teachings presented in the foregoing descriptions. Therefore, it is to be understood that the invention is not to be limited to the specific embodiments disclosed and that modifications are intended to be included within the scope of the appended claims. Although specific terms are employed herein, they are used in a generic and descriptive sense only and not for purposes of limitation.

What is claimed is:

1. A syringe calibrated to administer a predetermined medication of a predetermined medication strength according to at least two dosing instructions, comprising:
 a barrel having a first end, a second end, and an internal reservoir for containing the predetermined medication, the internal reservoir volumetrically calibrated according to the predetermined medication strength and the at least two dosing instructions:
 a plunger received through the first end of the barrel and movable relative thereto;
 a tip disposed at the second end of the barrel;
 a name or tradename of the predetermined medication marked on the syringe;
 the predetermined medication strength marked on the syringe;
 a first set of dosing indicia marked on the syringe for dosing the predetermined medication according to a first dosing instruction for a patient characteristic; and
 a second set of dosing indicia marked on the syringe for dosing the predetermined medication according to a second dosing instruction for a patient characteristic different from the first dosing instruction.

2. The syringe of claim 1, wherein the patient characteristic of the first dosing instruction and the patient characteristic of the second dosing instruction are the same patient characteristic, and wherein an amount of the predetermined medication according to the first dosing instruction is different from an amount of the predetermined medication according to the second dosing instruction.

3. The syringe of claim 1, wherein the patient characteristic of the first dosing instruction and the patient characteristic of the second dosing instruction are different patient characteristics.

4. The syringe of claim 1, wherein the syringe is further marked with a diluent name or diluent indicia measurement for reconstituting the predetermined medication.

5. The syringe of claim 1, wherein the patient characteristic of each of the first and second dosing instructions is expressed as body mass index (BMI), body surface area (BSA), or at least one variable used in any calculation of body mass index (BMI) or body surface area (BSA).

6. The syringe of claim 1, wherein at least one of the first and second sets of dosing indicia are graduated indicia comprising graduation lines.

7. The syringe of claim 1, wherein the tip is configured to be affixed to at least one of a hypodermic needle, elongated oral tip, transfer spike, medication container, diluent container, IV connection, IV bag, and a cap.

8. The syringe of claim 1, wherein the second end is threaded or comprises a molded feature.

9. The syringe of claim 1, wherein the tip comprises a key adapted to be received within a keyway of a container containing the predetermined medication.

10. The syringe of claim 1, wherein the syringe is marked with measurement indicia indicating at least one of volume and strength of the predetermined medication within the internal reservoir.

11. A pre-packaged kit, comprising:
 a medication container containing a volume of a medication, the medication container marked with the name or tradename of the medication and the medication strength of the medication contained in the medication container;
 at least two dosing instructions provided with the medication container, each of the at least two dosing instructions providing an instruction for dosing the medication according to a patient characteristic; and a dosing device comprising a barrel and a plunger, the barrel having an internal reservoir for containing a volume of the medication, the internal reservoir volumetrically calibrated according to the medication strength and the at least two dosing instructions, the dosing device marked with the name or tradename of the medication, the medication strength, and at least two sets of dosing indicia for dosing the medication according to the at least two dosing instructions.

12. The pre-packaged kit according to claim 11, wherein the at least two dosing instructions include a first dosing instruction for dosing the medication according to a first patient characteristic and a second dosing instruction for dosing the medication according to a second patient characteristic different from the first patient characteristic, and wherein doses of the medication according to the first and second dosing instructions are different amounts.

13. The pre-packaged kit according to claim 11, wherein the at least two dosing instructions include first and second dosing instructions for dosing the medication according to the same patient characteristic but in different amounts.

14. The pre-packaged kit according to claim 11, wherein the dosing device is a syringe.

15. The pre-packaged kit according to claim 11, wherein the at least two dosing instructions provide the amount of the predetermined medication indicated by a manufacturer of the predetermined medication, and wherein the at least two dosing instructions are marked on the medication container, kit packaging, or an instruction pamphlet.

16. The pre-packaged kit according to claim 11, further comprising a diluent container containing a volume of a diluent for reconstituting the medication.

17. The pre-packaged kit according to claim 11, wherein an end of the barrel includes a tip configured to engage at least one of a hypodermic needle, an elongated oral tip, a transfer spike, a container, an IV connection, an IV bag, and a cap.

18. The pre-packaged kit according to claim 17, wherein the tip is threaded or includes a molded feature.

19. The pre-packaged kit according to claim 17, wherein the tip is keyed and the medication container comprises a keyway for receiving the key.

20. The pre-packaged kit according to claim 11, wherein the dosing device is marked with measurement indicia indicating at least one of volume and strength of the predetermined medication within the internal reservoir.

* * * * *